US008921505B2

(12) United States Patent
Kim et al.

(10) Patent No.: US 8,921,505 B2
(45) Date of Patent: Dec. 30, 2014

(54) ULTRAVIOLET ABSORBING POLY (ORGANIC OXIDIZED SILICON) PARTICLES HAVING IMPROVED ULTRAVIOLET STABILITY, AND METHOD FOR PREPARING SAME

(75) Inventors: Young Baek Kim, Daejeon (KR); Goo Jin Jeong, Asan-si (KR); In Whan Kim, Busan (KR)

(73) Assignee: Nano and Micro Technologies Co., Ltd., Daejeon (KR)

( * ) Notice: Subject to any disclaimer, the term of this patent is extended or adjusted under 35 U.S.C. 154(b) by 0 days.

(21) Appl. No.: 13/810,177

(22) PCT Filed: Jul. 15, 2011

(86) PCT No.: PCT/KR2011/005243
§ 371 (c)(1),
(2), (4) Date: Jan. 14, 2013

(87) PCT Pub. No.: WO2012/008803
PCT Pub. Date: Jan. 19, 2012

(65) Prior Publication Data
US 2013/0109824 A1    May 2, 2013

(30) Foreign Application Priority Data

Jul. 15, 2010  (KR) .................. 10-2010-0068716

(51) Int. Cl.
| C08G 77/26 | (2006.01) |
| A61K 8/893 | (2006.01) |
| A61K 8/02 | (2006.01) |
| A61K 8/81 | (2006.01) |
| A61K 8/898 | (2006.01) |
| A61Q 17/04 | (2006.01) |
| C08G 77/00 | (2006.01) |

(52) U.S. Cl.
CPC .............. *A61K 8/898* (2013.01); *A61K 8/893* (2013.01); *A61K 8/025* (2013.01); *C08G 77/80* (2013.01); *A61K 8/8158* (2013.01); *A61K 2800/612* (2013.01); *C08G 77/26* (2013.01); *A61Q 17/04* (2013.01)
USPC .................. 528/43; 528/14; 528/19; 528/21; 528/41; 556/419; 556/436

(58) Field of Classification Search
None
See application file for complete search history.

(56) References Cited

U.S. PATENT DOCUMENTS

| 2006/0188456 A1* | 8/2006 | Ferenz et al. .................... 424/59 |
| 2007/0098653 A1* | 5/2007 | Tamasawa et al. ............... 424/59 |
| 2009/0232859 A1* | 9/2009 | Sakuta et al. .................. 424/401 |

FOREIGN PATENT DOCUMENTS

| JP | 7-267842 | 10/1995 |
| JP | 10-265356 | 10/1998 |
| JP | 2006-182688 | * 7/2006 |
| JP | 2006-182688 A | * 7/2006 |
| JP | 2008-308477 | 12/2008 |
| KR | 1991-0009820 | 2/1990 |
| KR | 10-2005-0105545 | 11/2005 |
| KR | 10-2006-0102225 | 9/2006 |
| WO | WO 2005/105028 | * 11/2005 |
| WO | WO 2008/138727 | * 11/2008 |

OTHER PUBLICATIONS

Machine-generated translation of JP 2006-182688 into the English language.*
Abstract for the article entitled "Preparation of Silica Gels Carrying Cinnamamido Groups and Their Protection Against Ultraviolet Rays" authored by Suetsugu et al. and published in Nippon Kagaku Kaishi (2000), 1, 33-36.*

* cited by examiner

*Primary Examiner* — Marc Zimmer
(74) *Attorney, Agent, or Firm* — Kile Park Reed & Houtteman PLLC

(57) ABSTRACT

The present invention relates to a method for preparing poly (organic oxidized silicon) particles having UV-absorbing groups, including reacting an organoalkoxysilane precursor having a UV-absorbing group selected from a group consisting of organotrialkoxysilane, diorganoalkoxysilane and a mixture thereof, in the presence of a base, with a silane compound selected from a group consisting of tetraalkoxysilane, alkyltrialkoxysilane, tetraalkoxysilane, aryltrialkoxysilane, dialkyldialkoxysilane, diaryldialkoxysilane, arylalkyldialkoxysilane and a mixture thereof, serving as a crosslinking regulator and UV stability enhancer, so as to prepare poly(organic oxidized silicon) particles selected from a group consisting of polysilsesquioxane, silsesquioxane-siloxane copolymer, silsesquioxane-silica copolymer, silsesquioxane-siloxane-silica copolymer and silsesquioxane-siloxane copolymer, having UV-absorbing groups. The poly (organic oxidized silicon) particles significantly solves the problem of poor UV stability, while maintaining UV absorption by the UV-absorbing group contained in the particles. Since the poly(organic oxidized silicon) particles having UV-absorbing groups do not exhibit white turbidity, they can be effectively used in cosmetics. In accordance with the present invention, the poly(organic oxidized silicon) particles having UV-absorbing groups can be prepared economically as compared to the existing methods.

12 Claims, 9 Drawing Sheets

ULTRAVIOLET ABSORBING POLY (ORGANIC OXIDIZED SILICON) PARTICLES HAVING IMPROVED ULTRAVIOLET STABILITY, AND METHOD FOR PREPARING SAME

BACKGROUND OF THE INVENTION

1. Field of the Invention

The present invention relates to UV-absorbing poly(organic oxidized silicon) particles having improved UV stability, which include polysilsesquioxane, polysiloxane and a silsesquioxane-siloxane-silica copolymer, and a method for preparing same.

2. Description of the Related Art

Ultraviolet (UV) light is known to negatively affect the skin, leading to burn or skin cancer. To prevent such skin damage, UV blockers containing organic or inorganic compounds that absorb UV and are less toxic to human body are used. Recently, use of UV blockers is increasing even in general-use cosmetics such as lipsticks where they were not used formerly.

At present, 17 kinds of UV blockers are approved in the US and 11 more kinds are approved in Europe. Among them, there are two particle type inorganic blockers: titania and zinc oxide. Organic blockers which are mostly liquid materials are known to penetrate into the skin without exception. Accordingly, inappropriate use may be harmful to the human body.

Since the two particle type inorganic blockers, i.e. titania and zinc oxide, are insoluble to water or general organic solvents, they are considered as safe without the possibility of penetrating into the human body. However, because they exhibit the white turbidity phenomenon of turning white when mixed with other substances, they are prepared into very small size of less than tens of nanometers to prevent the white turbidity phenomenon. However, regulations on nanoparticles smaller than 100 nm in size restrict this approach. Some of the actually used particles are smaller than 10 nm and it is reported that nanoparticles of this size may penetrate into human skin. The photochemical properties of titania change with particle size. Smaller particles tend to absorb rather than reflect light. Thus, whereas titania particles having a diameter approximately between hundreds of nanometers to micrometers reflect UV, titania nanoparticles absorb most of UV and emit electrons, thereby degrading nearby organic substances. Accordingly, titania nanoparticles are used as the so-called photocatalyst that degrades organic substances when UV is radiated. Since a severe problem may occur if the same reaction occurs on the skin, the titania nanoparticles for UV blocking are coated with various materials. However, the white turbidity problem is not solved thereby. For these reasons, titania is used in UV blockers in an amount less than 10% in most cases.

Cosmetics prepared by physically adding titania or zinc oxide to silica particles or polymer particles such as poly (methyl methacrylate) to prevent the white turbidity phenomenon and solve the nanoparticle problem are commercially available. However, the cosmetics obtained by this method have unsatisfactory lubricating and extending properties. When they are used in a larger amount to solve this problem, they cause the white turbidity problem again.

Polysilsesquioxane particles were prepared as one of poly (organic oxidized silicon) particles having p-methoxycinnamic acid groups. Since this particle has very good compatibility with organic and inorganic substances owing to the UV-absorbing p-methoxycinnamic acid group, it provides advantage in appearance to such an extent that petrolatum comprising 30 wt % of the particles with a particle diameter of about 1 μm do not exhibit white turbidity. Further, it provides good UV blocking effect such that a sun protection factor (SPF) of about 13 is achieved when it is included in an amount of about 10 wt %. In addition, it also substantially removes UVA owing to scattering and reflection of light by the particles, as compared to other organic UV blockers.

Despite the many advantages of the polysilsesquioxane particles having p-methoxycinnamic acid groups, they exhibit very low UV stability as compared to the liquid UV blocker octyl p-methoxycinnamic acid having the same UV-absorbing group, because the double bond of the cinnamic acid group undergoes [2+2] cyclization easily when exposed to sunlight or UV from a UV reactor. Although this problem can be solved indirectly to some extent by mixing with another UV blocker, the low UV stability is a very important defect for a UV-blocking substance, greatly limiting its application and commercialization. In addition, since polysilsesquioxane has a rigid crosslinked network structure with one silicon atom connected to another silicon atom via three oxygen atom, it has a rough feel.

Preparation of polysilsesquioxane spherical particles having N,N-dimethyl-p-aminobenzoic acid groups is much more complicated as compared to the spherical particles having p-methoxycinnamic acid groups. The preparation process is complex since the particles are not formed alone and other ingredients should be added together. In addition, the polysilsesquioxane having the N,N-dimethyl-p-aminobenzoic acid group also has much lower UV stability than N,N-dimethyl-p-aminobenzoic acid. Also, particles with rough feeling are obtained like other polysilsesquioxanes.

As such, UV-blocking particles prepared from polysilsesquioxane are difficult to be used for actual application due to the rough feeling and the fatal problem of low UV stability.

Soluble particles may also be used to improve UV stability while avoiding the skin penetration problem. It is known that skin penetration does not occur if the molecular weight is sufficiently large, for example about 1000 or larger.

Throughout the specification, a number of publications and patent documents are referred to and cited. The disclosure of the cited publications and patent documents is incorporated herein by reference in its entirety to more clearly describe the state of the related art and the present disclosure.

SUMMARY OF THE INVENTION

The inventors of the present invention have made efforts to prepare poly(organic oxidized silicon) particles of white color including one or more of polysilsesquioxane, polysiloxane and silica as UV blocker for cosmetics having improved UV-absorbing ability and UV stability. As a result, they have found that alkyltrialkoxysilane or aryltrialkoxysilane not only serves as crosslinking regulator but also improves UV stability and dialkyldialkoxysilane, diaryldialkoxysilane and arylalkyldialkoxysilane regulate hardness and improve UV stability. Further, they have found that when the preparation of particles is performed in the presence of a base, poly(organic oxidized silicon) particles having superior properties are prepared.

Accordingly, the present invention is directed to providing a method for preparing poly(organic oxidized silicon) particles having UV-absorbing groups, which have superior UV stability and improved sense of touch.

The present invention is also directed to providing poly (organic oxidized silicon) particles having UV-absorbing groups, which have superior UV stability and improved sense of touch.

The present invention is also directed to providing a cosmetic composition for blocking UV including poly(organic oxidized silicon) particles having UV-absorbing groups, which have superior UV stability and improved sense of touch.

Other objects and advantages of the present invention will become apparent from the detailed description to follow taken in conjugation with the appended claims and drawings.

DETAILED DESCRIPTION OF THIS INVENTION

Figure 1:
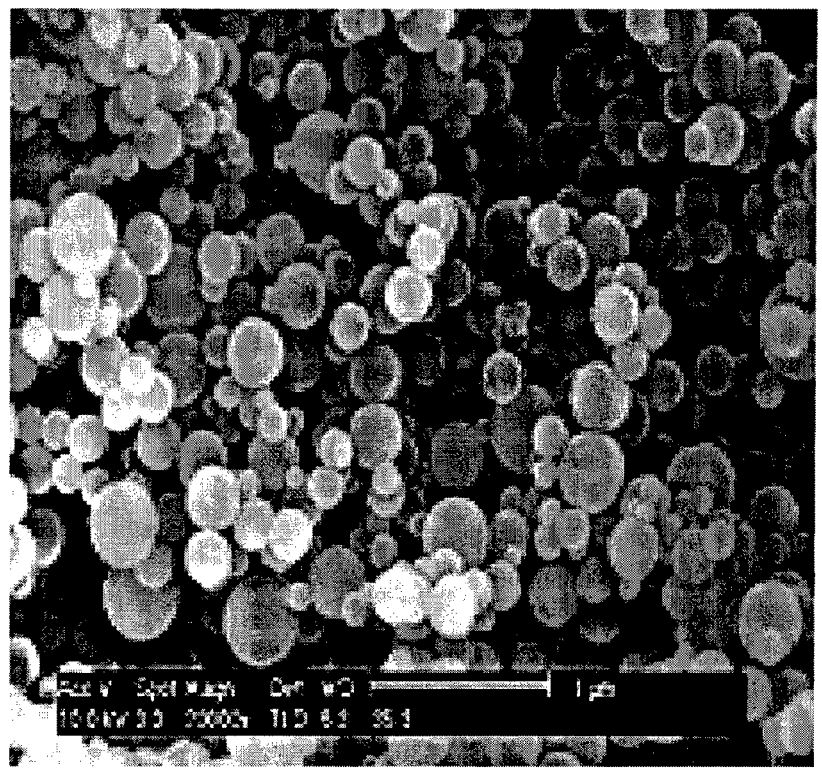
FIG. 1 is an SEM image of particles polymerized from 50 mol % of trimethoxysilylpropyl-p-methoxycinnamamide and 50 mol % of methyltrimethoxysilane in NaOH aqueous solution. Spherical particles can be observed.

In one aspect, the present invention provides a method for preparing poly(organic oxidized silicon) particles having UV-absorbing groups, including reacting an organoalkoxysilane precursor having a UV-absorbing group selected from a group consisting of organotrialkoxysilane, diorganoalkoxysilane and a mixture thereof, in the presence of a base, with a silane compound selected from a group consisting of tetraalkoxysilane, alkyltrialkoxysilane, tetraalkoxysilane, aryltrialkoxysilane, dialkyldialkoxysilane, diaryldialkoxysilane, arylalkyldialkoxysilane and a mixture thereof, serving as a crosslinking regulator and UV stability enhancer, so as to prepare poly(organic oxidized silicon) particles selected from a group consisting of polysilsesquioxane, silsesquioxane-siloxane copolymer, silsesquioxane-silica copolymer, silsesquioxane-siloxane-silica copolymer and silsesquioxane-siloxane copolymer, having UV-absorbing groups.

The inventors of the present invention have made efforts to prepare poly(organic oxidized silicon) particles of white color as UV blocker for cosmetics having improved UV-absorbing ability and UV stability. As a result, they have found that poly(organic oxidized silicon) particles with controlled degree of crosslinking and physical properties and improved UV stability can be prepared by reacting a polysilsesquioxane precursor, a polysiloxane precursor or a mixture thereof, which has a UV-absorbing group, with tetraalkoxysilane, alkyltrialkoxysilane, tetraalkoxysilane, aryltrialkoxysilane, dialkyldialkoxysilane, diaryldialkoxysilane, arylalkyldialkoxysilane or a mixture thereof in the presence of a base.

The present invention provides a method for preparing poly(organic oxidized silicon) particles having UV-absorbing groups, including one or more of polysilsesquioxane, polysiloxane and silica, from a polysilsesquioxane precursor, a polysiloxane precursor or a mixture thereof, which has a UV-absorbing group, by reacting a polysilsesquioxane precursor with alkyltrialkoxysilane, aryltrialkoxysilane, arylalkyldialkoxysilane or diaryldialkoxysilane, serving as a crosslinking regulator and UV stability enhancer, dialkyldialkoxysilane, diaryldialkoxysilane, arylalkyldialkoxysilane or tetraalkoxysilane, serving as a hardness regulator and crosslinking regulator, or a polysiloxane precursor having a UV-absorbing group, or by reacting a polysiloxane precursor having a UV-absorbing group with alkyltrialkoxysilane, aryltrialkoxysilane or tetraalkoxysilane, serving as a crosslinking regulator and UV stability enhancer, or a polysilsesquioxane precursor having a UV-absorbing group.

In accordance with the present invention, poly(organic oxidized silicon) particles having UV-absorbing groups are prepared by reacting, in the presence of a base, an organoalkoxysilane precursor having a UV-absorbing group selected from a group consisting of a polysilsesquioxane precursor (i.e., organotrialkoxysilane), a siloxane precursor (i.e., diorganoalkoxysilane) and a mixture thereof with a tetraalkoxysilane, alkyltrialkoxysilane, tetraalkoxysilane, aryltrialkoxysilane, dialkyldialkoxysilane, diaryldialkoxysilane, arylalkyldialkoxysilane or a mixture thereof, serving as a crosslinking regulator and UV stability enhancer.

The UV-absorbing group used in the present invention may be any UV-absorbing group known in the art. Specifically, the UV-absorbing group may be cinnamic acid or an alkoxy derivative thereof, benzoic acid or an ester thereof, p-aminobenzoic acid or a derivative thereof, benzylidenecamphor or a derivative thereof, isophthalylidenecamphor, terephthalylidenecamphor, salicylic acid or an ester thereof, a coumarin-based UV-absorbing group, 2-arylbenzimidazole, 2-arylbenzofuran, 2-arylbenzoxazole or 2-arylindole, more specifically cinnamic acid or an alkoxy derivative thereof, p-aminobenzoic acid or a derivative thereof or salicylic acid, most specifically p-methoxycinnamic acid, salicylic acid or N,N-dimethyl-p-aminobenzoic acid.

In an exemplary embodiment of the present invention, the poly(organic oxidized silicon) precursor having a UV-absorbing group used in the present invention includes various silane compounds having UV-absorbing groups attached thereto. More specifically, the poly(organic oxidized silicon) precursor having a UV-absorbing group may be alkyltrialkoxysilane, aryltrialkoxysilane, dialkyldialkoxysilane or diaryldialkoxysilane having a UV-absorbing group.

The alkyltrialkoxysilane used in the present invention as the silsesquioxane precursor may be $C_1$-$C_{10}$alkyltri$C_1$-$C_{10}$alkoxysilane, more specifically $C_1$-$C_5$alkyltri$C_1$-$C_5$alkoxysilane, most specifically $C_1$-$C_3$alkyltri$C_1$-$C_2$alkoxysilane. For example, the alkyltrialkoxysilane used in present invention may be propyltrimethoxysilane, ethyltrimethoxysilane, methyltrimethoxysilane, propyltriethoxysilane, ethyltriethoxysilane or methyltriethoxysilane, but is not limited thereto.

The aryltrialkoxysilane used in the present invention as the silsesquioxane precursor may be $C_5$-$C_{10}$aryltri$C_1$-$C_{10}$alkoxysilane, more specifically naphthyltri$C_1$-$C_2$alkoxysilane or phenyltri$C_1$-$C_5$alkoxysilane, most specifically phenyitriC$_1$-C$_2$alkoxysilane. For example, the aryltrialkoxysilane used in present invention may be naphthyltrimethoxysilane, naphthyltriethoxysilane, phenyltrimethoxysilane or phenyltriethoxysilane, but is not limited thereto.

The dialkyldialkoxysilane used in the present invention as the polysiloxane precursor may be diC$_1$-C$_{10}$alkyldiC$_1$-C$_{10}$alkoxysilane, more specifically C$_1$-C$_5$alkyldiC$_1$-C$_5$alkoxysilane, most specifically diC$_1$C$_3$alkyldiC$_1$-C$_2$alkoxysilane. For example, the dialkyldialkoxysilane used in present invention may be propylmethyldimethoxysilane, ethylmethyldimethoxysilane, dimethyldimethoxysilane, methylpropyldiethoxysilane, diethyldiethoxysilane or dimethyldiethoxysilane, but is not limited thereto.

The arylalkyldialkoxysilane used in the present invention as the siloxane precursor may be C$_5$-C$_{10}$arylC$_1$-C$_{10}$alkyldiC$_1$-C$_{10}$alkoxysilane, more specifically phenylC$_1$C$_5$alkyldiC$_1$-C$_5$alkoxysilane or naphthylC$_1$-C$_5$alkyldiC$_1$-C$_5$alkoxysilane, most specifically phenylmethyldiC$_1$C$_2$alkoxysilane. For example, the arylalkyldialkoxysilane used in present invention may be phenylmethyldimethoxysilane, phenylmethyldiethoxysilane, phenylethyldimethoxysilane or phenylethyldiethoxysilane, but is not limited thereto.

The diaryldialkoxysilane used in the present invention as the siloxane precursor may be diC$_5$-C$_{10}$aryidiC$_1$C$_{10}$alkoxysilane, more specifically dinaphthyidiC$_1$-C$_{10}$alkoxysilane or diphenyldiC$_1$-C$_{10}$alkoxysilane, most specifically diphenyldiC$_1$C$_2$alkoxysilane. For example, the diaryldialkoxysilane used in present invention may be diphenyldimethoxysilane or diphenyldiethoxysilane, but is not limited thereto.

In an exemplary embodiment of the present invention, the organoalkoxysilane precursor may be alkyltrialkoxysilane, aryltrialkoxysilane, dialkyldialkoxysilane or diaryldialkoxysilane having a covalently bonded UV-absorbing group.

In an exemplary embodiment of the present invention, the covalent bonding between the UV-absorbing group and the alkyltrialkoxysilane, dialkyldialkoxysilane, diaryldialkoxysilane or aryltrialkoxysilane may be an amide or ester bonding via the amino group or hydroxyl group at the end of the alkyltrialkoxysilane, dialkyldialkoxysilane, diaryldialkoxysilane or aryltrialkoxysilane. More specifically, the covalent bonding may be an amide bonding.

In an exemplary embodiment of the present invention, the poly(organic oxidized silicon) precursor having a UV-absorbing group may be trialkoxysilylsalicylamide, trialkoxysilylalkylsalicylate, alkyldialkoxysilylsalicylamide, alkyldialkoxysilylsalicylate, trialkoxysilylalkyl-p-methoxycinnamamide, alkyldialkoxysilylalkyl-p-methoxycinnamamide, trialkoxysilylaryl-p-methoxycinnamamide, trialkoxysilylalkyl-p-methoxycinnamate, alkyldialkoxysilylalkyl-p-methoxycinnamate, trialkoxysilylaryl-p-methoxycinnamate, (trialkoxysilylalkyl)-(p-N,N-dimethylamino)benzamide, (alkyldialkoxysilylalkyl)-(p-N,N-dimethylamino)benzamide, (trialkoxysilylaryl)-(p-N,N-dimethylamino)benzamide, (trialkoxysilylalkyl)-(p-N,N-dimethylamino)benzoate, (alkyldialkoxysilylalkyl)-(p-N,N-dimethylamino)benzoate or (trialkoxysilylaryl)-(p-N,N-dimethylamino) benzoate. The poly(organic oxidized silicon) precursor having a UV-absorbing group may be more specifically trialkoxysilylalkyl-p-methoxycinnamamide, alkyldialkoxysilylalkyl-p-methoxycinnamamide, trialkoxysilylaryl-p-methoxycinnamamide, (trialkoxysilylalkyl)-(p-N,N-dimethylamino)benzamide, (alkyldialkoxysilylalkyl)-(p-N,N-dimethylamino)benzamide or (alkyldialkoxysilylaryl)-(p-N,N-dimethylamino)benzamide, most specifically trialkoxysilylalkyl-p-methoxycinnamamide, (trialkoxysilylalkyl)-(p-N,N-dimethylamino)benzamide, alkyldialkoxysilylalkyl-p-methoxycinnamamide or (alkyldialkoxysilylalkyl)-(p-N,N-dimethyl-p-amino)benzamide.

In accordance with the method of the present invention, the silsesquioxane precursor having a UV-absorbing group is reacted with the alkyltrialkoxysilane, aryltrialkoxysilane, dialkyldialkoxysilane, diaryldialkoxysilane or alkylaryldialkoxysilane as a crosslinking regulator, hardness regulator and UV stability enhancer and the siloxane precursor having a UV-absorbing group in the presence of a base, and the polysiloxane precursor having a UV-absorbing group is reacted with the alkyltrialkoxysilane, aryltrialkoxysilane, dialkyldialkoxysilane, diaryldialkoxysilane or alkylaryldialkoxysilane as a crosslinking regulator and UV stability enhancer and the silsesquioxane precursor having a UV-absorbing group in the presence of a base.

As used herein, the term "crosslinking regulator" refers to a substance capable of controlling the physical properties and shape of a final product by regulating the degree of crosslinking of the product.

The base that can be used in the present invention may be any base known in the art (e.g. an organic base such as amine or an inorganic base such as NaOH).

In an exemplary embodiment of the present invention, the base suitable to be used for the method of the present invention is NaOH, KOH, Ca(OH)$_2$, Ba(OH)$_2$, CsOH, Sr(OH)$_2$, LiOH, RbOH, Mg(OH)$_2$, triethylamine or ammonia, more specifically a strong Inorganic base, further more specifically NaOH or KOH, most specifically NaOH.

One of the features of the present invention is the finding that the alkyltrialkoxysilane, aryltrialkoxysilane, dialkyldialkoxysilane or arylalkyldialkoxysilane used as the crosslinking regulator also serves as the UV stability enhancer. For example, if p-methoxycinnamic acid is used as fixed in solid state, the UV stability of p-methoxycinnamic acid decreases greatly. This problem may be remarkably reduced or resolved when aryltrialkoxysilane, alkyltrialkoxysilane, dialkyldialkoxysilane, arylalkyldialkoxysilane or aryltrialkoxysilane, particularly aryltrialkoxysilane and/or alkylaryldialkoxysilane is used.

The alkyltrialkoxysilane, aryltrialkoxysilane, dialkyldialkoxysilane diaryldialkoxysilane and arylalkyldialkoxysilane used as the crosslinking regulator and UV stability enhancer in the present invention may be any one known in the art.

In an exemplary embodiment of the present invention, the alkyltrialkoxysilane used as the crosslinking regulator and UV stability enhancer may be C$_1$C$_{10}$alkyitriC$_1$C$_{10}$alkoxysilane, more specifically C$_1$-C$_5$alkyltriC$_1$-C$_5$alkoxysilane, most specifically C$_1$C$_3$alkyltriC$_1$C$_2$alkoxysilane. For example, the alkyltrialkoxysilane used in the present invention may be propyltrimethoxysilane, ethyltrimethoxysilane, methyltrimethoxysilane, propyltriethoxysilane, ethyltriethoxysilane or methyltriethoxysilane, but is not limited thereto.

In an exemplary embodiment of the present invention, the dialkyldialkoxysilane used as the crosslinking regulator and UV stability enhancer may be C$_1$C$_{10}$dialkyldiC$_1$-C$_{10}$alkoxysilane, more specifically C$_1$C$_5$dialkyldiC$_1$-C$_5$alkoxysilane, most specifically C$_1$-C$_3$dialkyldiC$_1$-C$_2$alkoxysilane. For example, the dialkyldialkoxysilane used in the present invention may be dimethyldimethoxysilane, diethyldimethoxysilane, dipropyldimethoxysilane, methylvinyldimethoxysilane, dipropyldiethoxysilane, diethyldiethoxysilane or dimethyldiethoxysilane, but is not limited thereto.

In an exemplary embodiment of the present invention, the aryltrialkoxysilane used as the crosslinking regulator and UV stability enhancer may be $C_5$-$C_{10}$aryltri$C_1$-$C_{10}$alkoxysilane, more specifically phenyltri-$C_1$-$C_5$alkoxysilane, most specifically phenyltri$C_1$-$C_2$alkoxysilane. For example, the aryltrialkoxysilane used in the present invention may be phenyltrimethoxysilane or phenyltriethoxysilane, but is not limited thereto.

In an exemplary embodiment of the present invention, the arylalkyldialkoxysilane used as the crosslinking regulator and UV stability enhancer may be $C_5$-$C_{10}$aryl$C_1$-$C_{10}$alkyldi$C_1$-$C_{10}$alkoxysilane, more specifically phenyl$C_1$-$C_5$alkyldi$C_1$-$C_5$alkoxysilane or naphthyl$C_1$-$C_5$alkyldi$C_1$-$C_5$alkoxysilane, most specifically phenyimethyldi$C_1$-$C_2$alkoxysilane. For example, the arylalkyldialkoxysilane used in the present invention may be phenylmethyldimethoxysilane, phenylmethyldiethoxysilane, phenylethyldimethoxysilane or phenylethyldiethoxysilane, but is not limited thereto.

In an exemplary embodiment of the present invention, the organoalkoxysilane precursor may be alkyltrialkoxysilane or aryltrialkoxysilane having a UV-absorbing group, the crosslinking regulator and UV stability enhancer may be alkyltrialkoxysilane or aryltrialkoxysilane, and the poly(organic oxidized silicon) having a UV-absorbing group may be polysilsesquioxane having a UV-absorbing group.

The alkyltrialkoxysilane, aryltrialkoxysilane, arylalkyldialkoxysilane, dialkyldialkoxysilane and diphenyldialkoxysilane used in the present invention as the crosslinking regulator and UV stability enhancer also exhibit superior function as an inhibitor of white turbidity.

The tetraalkoxysilane used in the present invention as the crosslinking regulator and hardness regulator may be tetraethoxysilane or tetramethoxysilane, but is not limited thereto.

If p-methoxycinnamic acid is used as fixed in solid state (e.g., particulate or powder state), the UV stability of p-methoxycinnamic acid decreases greatly because the double bond of the cinnamic acid group undergoes [2+2] cyclization easily when exposed to sunlight or UV than when it is in free molecular form. The alkyltrialkoxysilane and aryltrialkoxysilane used in the present invention as the crosslinking regulator and UV stability enhancer, particularly the aryltrialkoxysilane, solves this problem and prevents white turbidity. The alkyltrialkoxysilane or aryltrialkoxysilane used in the present invention as the crosslinking regulator and UV stability enhancer, particularly the aryltrialkoxysilane, does not absorb light in the UVB region of 280-320 nm as it is but, when copolymerized with trialkoxysilyl-p-methoxycinnamamide, affects slightly or increases UV absorption of the resulting particle in the range of 280-320 nm even at very high content. This surprising effect cannot be easily expected from the common knowledge in the field of photoreaction.

When (trialkoxysilylalkyl)-(p-N,N-dimethyl-p-amino)benzamide, specifically (trimethoxysilylpropyl)-(p-N,N-dimethyl-p-amino)benzamide, is used as the silsesquioxane precursor having a UV-absorbing group, alkyltrialkoxysilane, specifically ethyltrimethoxysilane, propyltrimethoxysilane or methyltrimethoxysilane, may be very suitable as the crosslinking regulator and UV stability enhancer.

Since the preparation of polysilsesquioxane spherical particles having N,N-dimethyl-p-aminobenzoic acid groups is much more complicated as compared to the spherical particles having p-methoxycinnamic acid groups and other ingredients should be added together because the particles are not formed alone, the UV-absorbing ability may be negatively affected. This problem may be minimized by using the alkyltrialkoxysilane or aryltrialkoxysilane.

The alkyltrialkoxysilane and aryltrialkoxysilane used in the present invention as the crosslinking regulator and UV stability enhancer, particularly the alkyltrialkoxysilane, solves the problem of the N,N-dimethyl-p-aminobenzoic acid described above and greatly improves the applicability of the N,N-dimethyl-p-aminobenzoic acid as the UV blocker.

When trialkoxysilylalkyl-p-methoxycinnamamide is used as the silsesquioxane precursor having a UV-absorbing group, a mixture of aryltrialkoxysilane and alkyltrialkoxysilane may be used as the crosslinking regulator and UV stability enhancer. Interestingly, a very superior effect of UV stability improvement and white turbidity prevention is achieved without sacrificing UV-absorbing ability in this case.

In the preparation method of the present invention, the amount of the silsesquioxane precursor having a UV-absorbing group and the crosslinking regulator is not particularly limited. For example, they may be used at a weight ratio from 100:1 to 1:5.

When UV-absorbing particles are prepared from methyldimethoxysilylpropyl-p-methoxycinnamamide and methyldimethoxysilylpropyl-(p-N,N-dimethylaminobenzamide), methyltrimethoxysilane and phenyltrimethoxysilane exhibit remarkable effect as the crosslinking regulator and UV stability enhancer and phenylmethyldimethoxysilane exhibits remarkable effect as the UV stability enhancer.

In another aspect, the present invention provides a method for preparing poly(organic oxidized silicon) particles having UV-absorbing groups with improved sense of touch and UV stability, including reacting a poly(organic oxidized silicon) precursor having a UV-absorbing group with alkyltrialkoxysilane, aryltrialkoxysilane, dialkyldialkoxysilane, alkylaryldialkoxysilane or tetraalkoxysilane as a crosslinking regulator, hardness regulator and UV stability enhancer in the presence of a base.

The reaction of the present invention may be performed in a medium including: an alcohol solvent such as methanol, ethanol, isopropanol, butanol, etc.; an ether alcohol solvent such as ethylene glycol methyl ether, ethylene glycol ethyl ether, propylene glycol ethyl ether, etc.; an ether solvent such as diethyl ether, tetrahydrofuran, dioxane, etc.; a ketone solvent such as acetone, methyl ethyl ketone, etc.; water; and a mixture thereof. Use of water as the medium may be advantageous in terms of cost and easiness of handling.

Specifically, the reaction of the present invention may be performed at 20-80° C.

In an exemplary embodiment of the present invention, the method of the present invention may further include, after the reaction of the poly(organic oxidized silicon) precursor with the crosslinking regulator and crosslinking regulator, adjusting pH to 1-8, more specifically to 5-7, further more specifically to 5-6. By neutralizing the reaction product obtained in the presence of a base through the pH adjustment, poly(organic oxidized silicon) remaining dissolved in the presence of a base may be precipitated and, thus, reaction yield may be increased.

In accordance with the present invention, the size of the poly(organic oxidized silicon) particles may be controlled from tens of nanometers to tens of micrometers by controlling the amount of the silsesquioxane precursor and the crosslinking regulator, the amount of the solvent (e.g., water), reaction time, the amount of the base, or the like. Further, oligomers in the form of amorphous solid oil or liquid oil may be prepared by controlling molecular weight. Specifically, the polysilsesquioxane particles prepared by the present invention may have a size of several micrometers.

The poly(organic oxidized silicon) particles having UV-absorbing groups prepared by the present invention may be used to block UV or to utilize fluorescence from UV. More specifically, they may be used as UV-protecting agents with improved stability in UV-blocking cosmetics, bioscience products, fiber, rubber, paper, leather, plastics and food.

In accordance with the present invention, poly(organic oxidized silicon) particles that are not absorbed into the human body, exhibit no white turbidity owing to strong affinity with organic substances and have improved UV stability and UV-blocking effect can be prepared economically.

In another aspect, the present invention provides poly(organic oxidized silicon) particles having UV-absorbing groups prepared by the method of the present invention described in detail above.

In another aspect, the present invention provides a cosmetic composition for blocking UV, including the poly(organic oxidized silicon) particles having UV-absorbing groups described in detail above.

The cosmetic composition of the present invention may further include, in addition to the poly(organic oxidized silicon) particles having UV-absorbing groups as active ingredient, the ingredients commonly used in cosmetic compositions. They include, for example, common adjuvants such as stabilizer, solubilizer, vitamin, pigment and fragrance and carriers.

The cosmetic composition for blocking UV of the present invention may be prepared into any formulation commonly prepared in the art. Examples may include solution, suspension, emulsion, paste, gel, cream, lotion, powder, soap, surfactant-containing cleanser, oil, powder foundation, emulsion foundation, wax foundation, spray, etc., but are not limited thereto. More specifically, it may be prepared into skin lotion, milk lotion, nourishing cream, massage cream, essence, eye cream, cleansing cream, cleansing foam, cleansing water, pack, spray or powder.

If the formulation of the present invention is paste, cream or gel, it may contain, as carrier components, animal oil, vegetable oil, wax, paraffin, starch, tragacanth, cellulose derivatives, polyethylene glycol, silicone, bentonite, silica, talc or zinc oxide.

If the formulation of the present invention is powder or spray, it may contain, as carrier components, lactose, talc, silica, aluminum hydroxide, calcium silicate or polyamide powder. Particularly, if it is spray, it may additionally contain a propellant such as chlorofluorohydrocarbon, propane/butane or dimethyl ether.

If the formulation of the present invention is solution or emulsion, it may contain, as carrier components, a solvent, a solubilizer or an emulsifier, for example, water, ethanol, isopropanol, ethyl carbonate, ethyl acetate, benzyl alcohol, benzyl benzoate, propylene glycol, 1,3-butyl glycol oil, glycerol fatty ester, polyethylene glycol or sorbitan fatty acid ester.

If the formulation of the present invention is suspension, it may contain, as carrier components, a liquid diluent such as water, ethanol or propylene glycol, a suspending agent such as ethoxylated isostearyl alcohol, polyoxyethylene sorbitol ester, polyoxyethylene sorbitan ester, microcrystalline cellulose, aluminum metahydroxide, bentonite, agar or tragacanth.

If the formulation of the present invention is surfactant-containing cleanser, it may contain, as carrier components, aliphatic alcohol sulfate, aliphatic alcohol ether sulfate, sulfosuccinic monoester, isethionate, imidazolium derivatives, methyl taurate, sarcosinate, fatty acid amide ether sulfate, alkyl amidobetaine, aliphatic alcohol, fatty acid glyceride, fatty acid diethanolamide, vegetable oil, lanolin derivatives or ethoxylated glycerol fatty acid ester.

When the composition of the present invention is prepared as a pharmaceutical composition, it may contain a pharmaceutically acceptable carrier. For example, it may contain lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxybenzoate, talc, magnesium stearate and/or mineral oil.

The features and advantages of this invention are will be summarized as follows:

(a) The present invention provides a novel method for preparing poly(organic oxidized silicon) particles having UV-absorbing groups, having very superior sense of touch, UV-absorbing ability and UV stability.

(b) The poly(organic oxidized silicon) particles of the present invention maintain UV-absorbing ability even when the content of the UV-absorbing groups absorbing UV of 280-320 nm is very low and remarkably improves UV stability of the particles having the UV-absorbing groups 100%.

(c) Since the poly(organic oxidized silicon) particles having UV-absorbing groups of the present invention exhibit no white turbidity, they may be usefully applied to cosmetics.

(d) In accordance with the present invention, poly(organic oxidized silicon) particles having UV-absorbing groups can be prepared very economically as compared to the existing methods since content of the expensive precursor having a UV-absorbing group can be greatly decreased and an inexpensive precursor can be used instead.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Synthesis of Trimethoxysilylpropyl-P-Methoxycinnamamide 100 g of p-methoxycinnamic acid (Aldrich) was dissolved in 500 mL of toluene and 100 mL of thionyl chloride (Oriental Chemical Industries) was slowly added thereto. After stirring at 60° C. for 18 hours, all volatile substances were removed by evaporation under reduced pressure while maintaining temperature at 80° C. or lower. After adding 500 mL of toluene to the product, a mixture of 80 g of triethylamine (Aldrich) and 100 g of 3-aminopropyltrimethoxysilane (Aldrich) was slowly added dropwsie to the resulting solution. Thus obtained mixture was stirred continuously for about 5 hours and cooled to room temperature. After removing the formed salt by filtration under reduced pressure and removing toluene under reduced pressure, trimethoxysilylpropyl-p-methoxycinnamamide was obtained. Purity of the synthesized precursor was measured by silica thin-layer chromatography.

Example 2

Preparation of UV-Blocking Particles Using Trimethoxysilylpropyl-P-Methoxycinnamamide 100 g of trimethoxysilylpropyl-p-methoxycinnamamide was liquefied by heating and 5 L of water heated to about 60°

C. was slowly added while vigorously stirring. After adding 50 mL of triethylamine (Aldrich) to the resulting colloidal solution, the solution was stirred for 3 hours while maintaining temperature. After cooling to room temperature and stirring for at least 12 hours, the pH of the mixture was adjusted to about 5 by adding 10% hydrochloric acid. After further stirring for about 2 hours, particles were collected by filtering. Morphology of thus obtained spherical particles was observed by scanning electron microscopy (SEM) (FIG. 1).

Example 3

Figure 2:
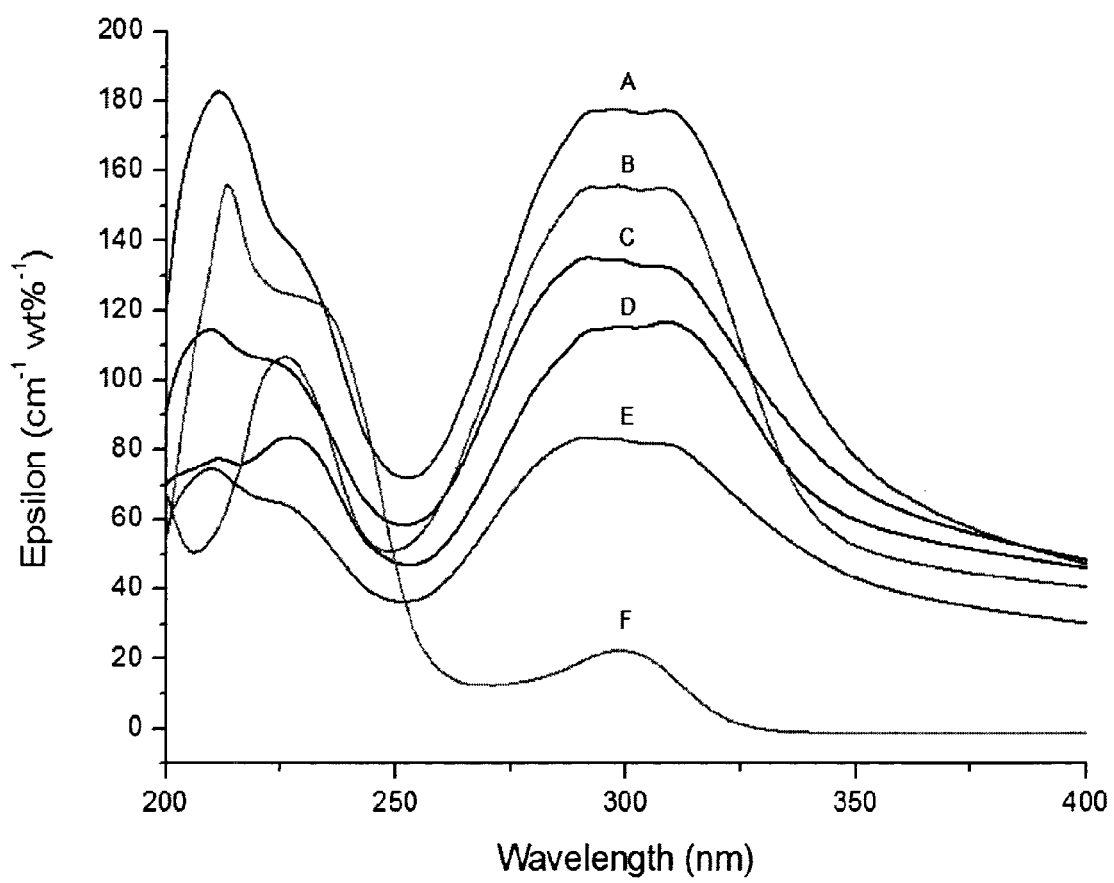
FIG. 2 shows UV/VIS spectra of various particles prepared in Examples.

UV Absorption Spectrum of UV-Blocking Particles Prepared from Trimethoxysilylpropyl-P-Methoxycinnamamide The particles prepared in Example 2 were diluted in methanol to 0.01 wt % and absorbance was measured at 250-600 nm using a UV spectrometer (Shimadzu). A spectrum almost similar to that of p-methoxycinnamic acid was obtained (FIG. 2, B).

Example 4

UV Stability of Particles Prepared from Trimethoxysilylpropyl-P-Methoxycinnamamide and Ethylhexyl-P-Methoxycinnamate 1

The particles prepared in Example 2 were thinly spread on a Petri dish and exposed to sunlight for a day. Ethylhexyl-p-methoxycinnamate was thinly spread on a Petri dish and exposed to sunlight under the same condition. The particles were recovered and absorbance was measured as in Example 3. The UV absorption spectrum of ethylhexyl-p-methoxycinnamate was obtained after diluting to 0.003 mM. After exposure to UV, the particles exhibited very poor UV stability of with about 50% of initial absorbance, whereas ethylhexyl-p-methoxycinnamate showed about 95% of initial absorbance.

Example 5

UV Stability of Particles Prepared from Trimethoxysilylpropyl-P-Methoxycinnamamide and Ethylhexyl-P-Methoxycinnamate 2

Figure 3:
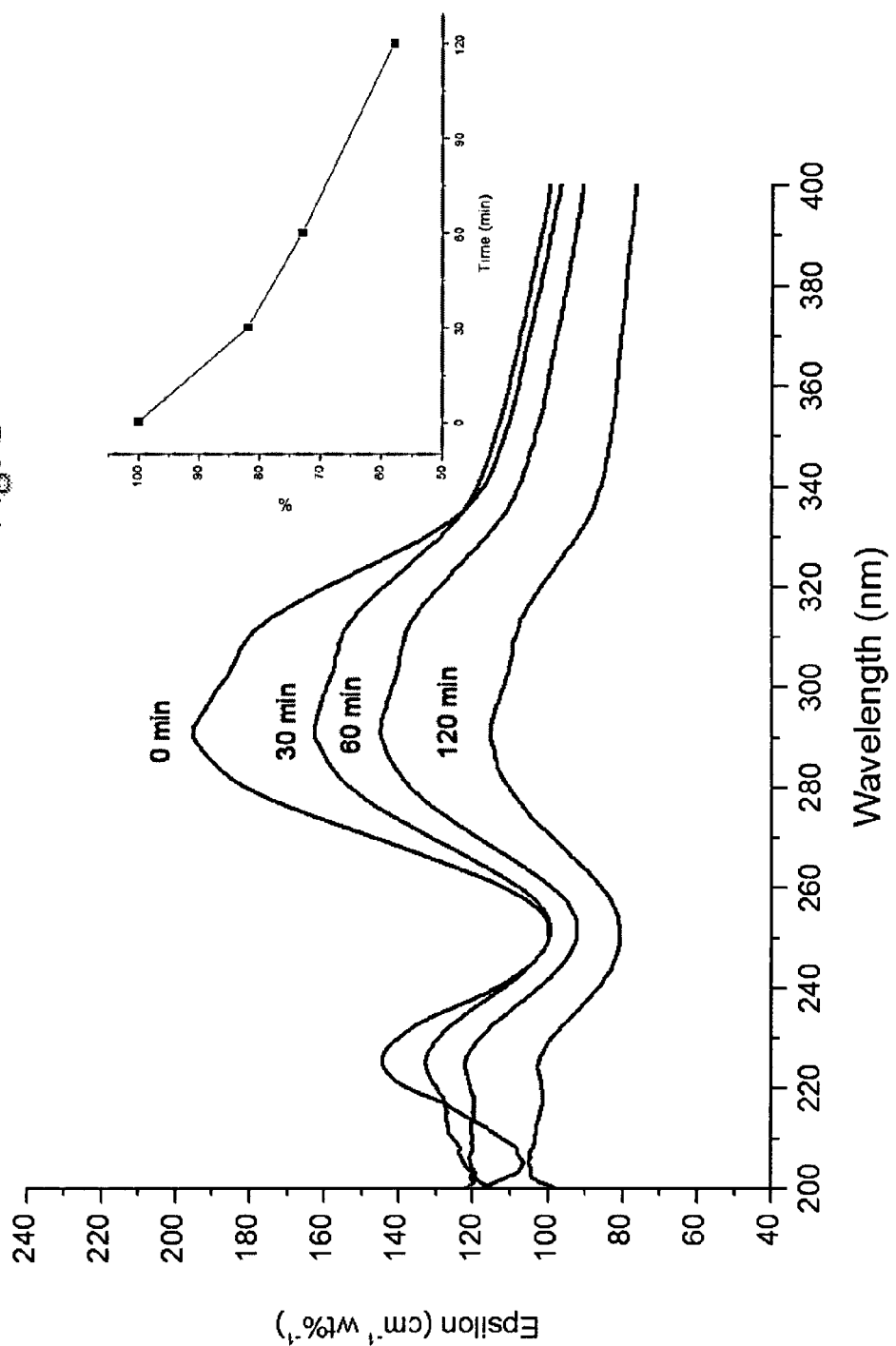
FIG. 3 shows change in absorbance of particles prepared from trimethoxysilylpropyl-p-methoxycinnamamide upon irradiation of UV.

The particles prepared in Example 2 were thinly spread on a Petri dish. While irradiating UV inside a UV reactor using a mercury lamp, sample was taken with 30-minute intervals and absorbance was measured as in Example 3. UV was also irradiated to ethylhexyl-p-methoxycinnamate in the same manner. The intensity of UVB arriving at the sample distant from the lamp by about 20 cm was about 200 mW/cm2. After irradiation of UV for 30, 60 and 120 minutes, the absorbance of the particles was 82%, 73% and 57% of initial absorbance. The absorbance of ethylhexyl-p-methoxycinnamate irradiated with UV for 120 minutes under the same condition was 70% of initial absorbance. Accordingly, it can be seen that the particles have worse UV stability than ethylhexyl-p-methoxycinnamate (FIG. 3).

Example 6

Synthesis of (Trimethoxysilylpropyl)-(P-N,N-Dimethylamino)Benzamide 50 g of p-N,N-dimethylaminobenzoic acid (Aldrich) was cautiously added to 500 mL of toluene under reflux. 50 g of thionyl chloride (Oriental Chemical Industries) was slowly dropped from a dropping funnel through a reflux condenser. After refluxing the mixture for 16 hours, all volatile substances were evaporated under reduced pressure. After adding 200 mL of toluene to the product, a mixture of 60 g of 3-aminopropyltrimethoxysilane (Acros) and 40 g of triethylamine (Aldrich) was slowly added dropwsie to the resulting transparent solution. Thus obtained mixture was stirred for 6 hours and the formed salt was removed by filtering under reduced pressure. After evaporating toluene from the solution, thus obtained product was identified by silica thin-layer chromatography.

Example 7

Preparation of Particles Using (Trimethoxysilylpropyl)-(P-N,N-Dimethylamino)Benzamide 10 g of the product obtained in Example 6 was added to 200 mL of 1% NaOH aqueous solution at 60° C. while vigorously stirring. After stirring the resulting colloidal solution for 12 hours, the pH of the solution was adjusted to 5-6 using 10% HCl. After further stirring for about 2 hours, particles were obtained by filtering. The obtained particles were soluble in ethanol and were inappropriate for insoluble UV-blocking particles.

Example 8

Synthesis of (Methyldimethoxysilylpropyl)-(P-N,N-Dimethylamino)Benzamide 50 g of p-N,N-dimethylaminobenzoic acid (Aldrich) was cautiously added to 500 mL of toluene under reflux. 50 g of thionyl chloride (Oriental Chemical Industries) was slowly dropped from a dropping funnel through a reflux condenser. After refluxing the mixture for 16 hours, all volatile substances were evaporated under reduced pressure. After adding 200 mL of toluene to the product, a mixture of 50 g of methyldimethoxy-3-aminopropylsilane (Aldrich) and 40 g of triethylamine (Aldrich) was slowly added dropwise. Thus obtained mixture was stirred for 6 hours and the formed salt was removed by filtering under reduced pressure. After evaporating toluene from the solution, thus obtained product was identified by silica thin-layer chromatography.

Example 9

Preparation of Particles Using (Methyldimethoxysilylpropyl)-(P-N,N-Dimethylamino)Benzamide 10 g of the precursor obtained in Example 8 was dissolved in 100 mL of ethanol. 150 mL of water was added to the resulting solution while stirring to obtain a colloid. A brighter-colored colloid could be obtained by adding 50 mL of 10% NaOH aqueous solution. Through centrifugation, a product was obtained in the form of sticky oil. Although oil-type oligomers having UV-blocking ability could be prepared, particles were not obtained.

Example 10

Synthesis of Methyldimethoxysilylpropyl-P-Methoxycinnamamide 100 g of p-methoxycinnamic acid was dissolved in 500 mL of toluene and 100 mL of thionyl chloride was slowly added thereto. After stirring at 60° C. for 18 hours, all volatile substances were removed by evaporation under reduced pressure while maintaining temperature at 80° C. or lower. After adding 500 mL of toluene to the product, a mixture of 80 g of triethylamine and 80 g of 3-aminopropylmethyldimethoxysilane (Acros) was slowly added to the resulting solution. Thus obtained mixture was stirred continuously for about 5 hours and cooled to room temperature. After removing the formed salt by filtration under reduced pressure and removing toluene under reduced pressure, methyldimethoxysilylpropyl-p-methoxycinnamamide was obtained. Purity of the synthesized precursor was measured by silica thin-layer chromatography.

Example 11

Preparation of Particles Using Methyldimethoxysilylpropyl-P-Methoxycinnamamide 10 g of the precursor obtained in Example 10 was dissolved in 20 g of ethanol and dispersed in 200 mL of water to obtain a colloid. A brighter-colored colloid was obtained by adding 5 mL of triethylamine while stirring well. Through centrifugation, a product was obtained in the form of liquid with low viscosity. Although oligomers could be prepared, insoluble particles were not obtained.

Example 12

Preparation of Particles Using Trimethoxysilylpropyl-P-Methoxycinnamamide and (Trimethoxysilylpropyl)-(P-N,N-Dimethylamino)Benzamide 10 g of trimethoxysilylpropyl-p-methoxycinnamamide and 10 g of (trimethoxysilylpropyl)-(p-N,N-dimethylamino)benzamide were dissolved in 30 mL of ethanol and mixed with 300 mL of water which was being vigorously stirred at room temperature to obtain a colloid. After adding 30 mL of 10% NaOH solution and stirring continuously for 6 hours, particles were obtained by filtering.

Example 13

Preparation of Particles Using Trimethoxysilylpropyl-P-Methoxycinnamamide and Methyldimethoxysilylpropyl-P-Methoxycinnamamide 10 g of methyldimethoxysilylpropyl-p-methoxycinnamamide and 10 g of trimethoxysilylpropyl-p-methoxycinnamamide were mixed with 1 L of 0.1% NaOH aqueous solution at 60° C. to obtain a colloid. After stirring the colloid for 12 hours, pH was adjusted to 5-6 using 10 wt % HCl. The product was further stirred for 2 hours and filtered to collect particles.

Example 14

UV Stability of Particles Prepared Using Trimethoxysilylpropyl-P-Methoxycinnamamide and (Trimethoxysilylpropyl)-(P-N,N-Dimethylamino)Benzamide After irradiation of UV for 30 minutes, 1 hour, 2 hours and 3 hours, the absorbance of the particles prepared in Example 12 was measured as in Example 5. The absorbance was 84%, 75%, 70% and 65% of initial absorbance. Accordingly, it can be seen that the particles have slightly improved UV stability as compared to the particles prepared in Example 2.

Example 15

Preparation of Particles Using Trimethoxysilylpropyl-P-Methoxycinnamamide and Propyltrimethoxysilane 10 g of trimethoxysilylpropyl-p-methoxycinnamamide and 10 g of propyltrimethoxysilane (Aldrich) were mixed and added to 1 L of 1 wt % NaOH aqueous solution heated to 60° C. while vigorously stirring. The resulting colloid was stirred at room temperature for 12 hours and pH was adjusted to 5-6 using 10 wt % HCl. After stirring for 2 hours, particles were recovered by filtering.

Example 16

Preparation of Particles Using Trimethoxysilylpropyl-P-Methoxycinnamamide and Tetraethoxysilane 5 g of trimethoxysilylpropyl-p-methoxycinnamamide and 5 g of tetraethoxysilane (Aldrich) were mixed to prepare a homogeneous solution and added to 1 L of 1 wt % NaOH aqueous solution at room temperature while vigorously stirring. After stirring the resulting mixture for 18 hours at room temperature and adjusting pH to 5-6, particles were recovered by filtering. The obtained particles were harder than the particles including no tetraethoxysilane.

Example 17

UV Absorption Spectrum of Particles Prepared Using Trimethoxysilylpropyl-P-Methoxycinnamamide and Propyltrimethoxysilane UV spectrum of the particles prepared in Example 15 was measured as in Example 3. They exhibited about 25% decreased UV spectrum as compared to the colloid prepared from trimethoxysilylpropyl-p-methoxycinnamamide only at the same concentration (FIG. 2, D).

Example 18

UV Stability of Particles Prepared Using Trimethoxysilylpropyl-P-Methoxycinnamamide and Propyltrimethoxysilane UV absorbance of the particles prepared in Example 15 was measured as in Example 5 after irradiation of UV for 30 minutes, 1 hour and 2 hours. They exhibited slightly improved UV stability, with 90%, 70% and 60% of initial absorbance, respectively.

Example 19

Figure 4:
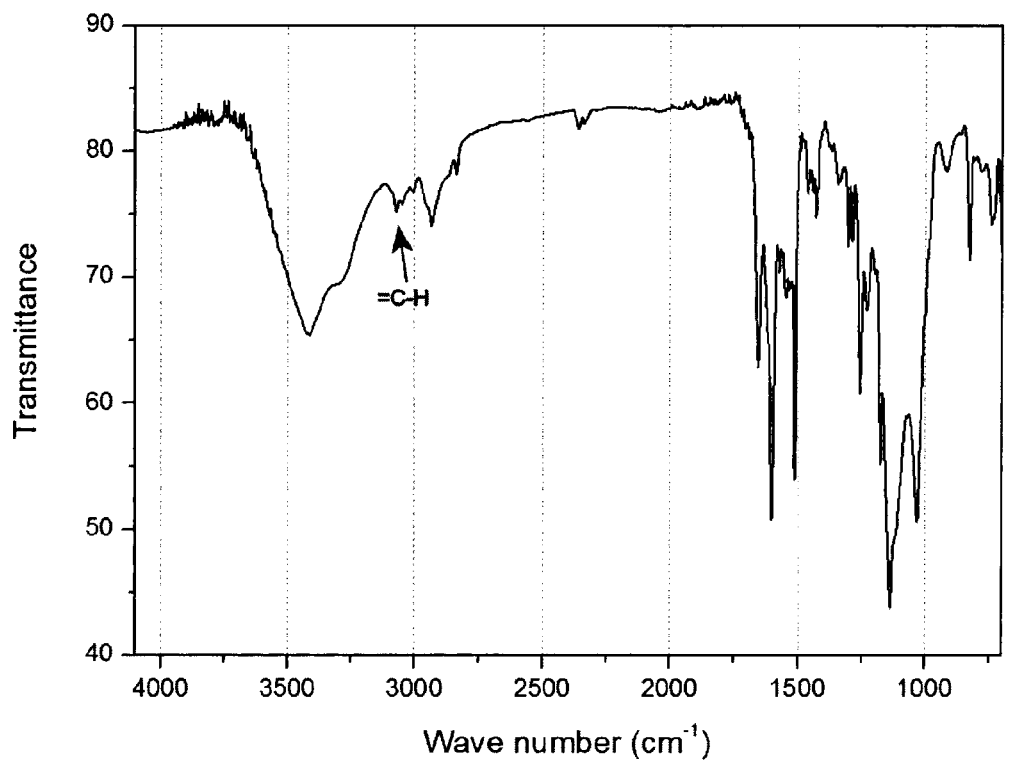
FIG. 4 shows IR spectrum of particles prepared from trimethoxysilylpropyl-p-methoxycinnamamide and phenyltrimethoxysilane.
Figure 5:
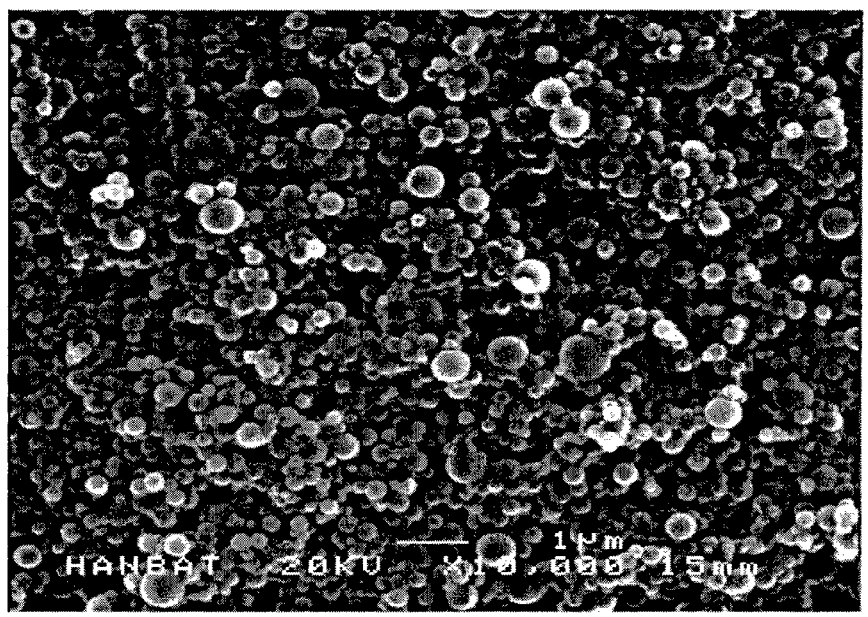
FIG. 5 is an SEM image of particles prepared from trimethoxysilylpropyl-p-methoxycinnamamide and phenyltrimethoxysilane.

Preparation of Particles Using Trimethoxysilylpropyl-P-Methoxycinnamamide and Phenyltrimethoxysilane 10 g of trimethoxysilylpropyl-p-methoxycinnamamide and 10 g of phenyltrimethoxysilane (Aldrich) were mixed and added to 1 L of 0.1% NaOH aqueous solution heated to 60° C. The resulting colloidal solution was stirred for 12 hours and pH was adjusted to 5-6 using 10 wt % HCl. After further stirring for 2 hours, particles were recovered by filtering. Increased phenyl groups in the obtained particles could be identified from IR spectrum (FIG. 4). Also, morphology of the particles was observed by SEM (FIG. 5).

Example 20

UV Absorption Spectrum of Particles Prepared Using Trimethoxysilylpropyl-P-Methoxycinnamamide and Phenyltrimethoxysilane UV spectrum of the particles obtained in Example 19 was measured as in Example 3. The spectrum was the same as that of the particles obtained in Example 1 but the obtained particles exhibited a slightly higher extinction coefficient (FIG. 2, A).

Example 21

Figure 6:
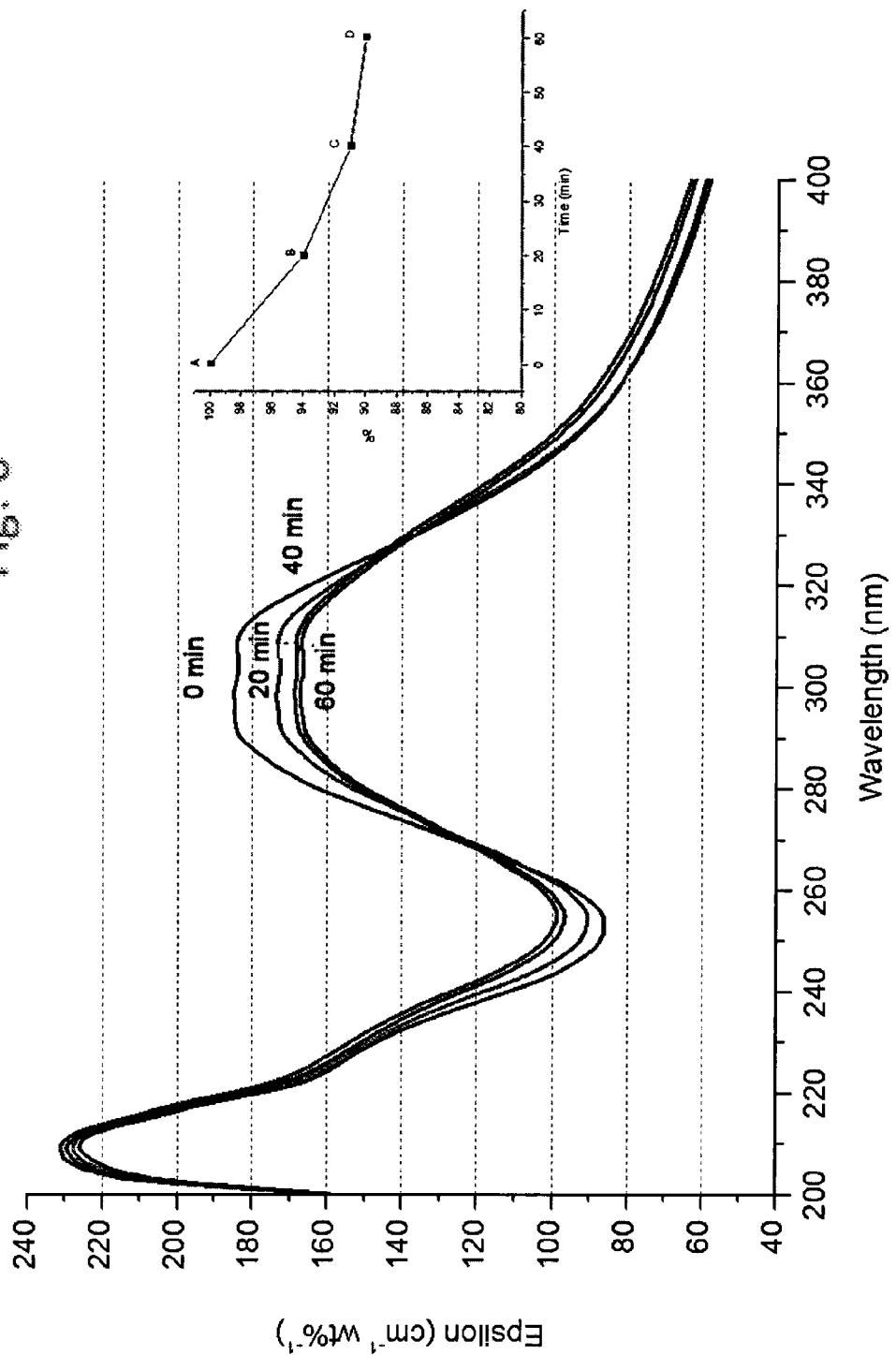
FIG. 6 shows an absorbance analysis result of particles prepared from trimethoxysilylpropyl-p-methoxycinnamamide and phenyltrimethoxysilane showing their UV stability.

UV Stability of Particles Prepared Using Trimethoxysilylpropyl-P-Methoxycinnamamide and Phenyltrimethoxysilane UV absorbance of the particles obtained in Example 19 was measured as in Example 5 after irradiation of UV for 20 minutes, 40 minutes and 60 minutes. They exhibited remarkably improved UV stability as compared to those obtained in Example 1, with 94%, 92% and 91% of initial absorbance, respectively (FIG. 6).

Example 22

Preparation of Particles Using Trimethoxysilylpropyl-P-Methoxycinnamamide and Methyltrimethoxysilane 10 g of trimethoxysilylpropyl-p-methoxycinnamamide and 5 g of methyltrimethoxysilane (Aldrich) were mixed. The mixture was added to 800 mL of 1 wt % NaOH aqueous solution heated to 60° C. while vigorously stirring. The resulting colloid was stirred for 12 hours at room temperature and pH was adjusted to 5-6 using 10 wt % HCl. After stirring for 2 hours, particles were recovered by filtering.

Example 23

UV Stability of Particles Prepared Using Trimethoxysilylpropyl-P-Methoxycinnamamide and Methyltrimethoxysilane UV absorbance of the particles obtained in Example 21 was measured as in Example 5 after exposure to UV for 1, 2 and 3 hours. They exhibited no significant difference in UV stability, with 60%, 50% and 40% of initial absorbance, respectively.

Example 24

Preparation of Particles Using Trimethoxysilylpropyl (P-N,N-Dimethylamino)Benzamide and Phenyltrimethoxysilane 10 g of (trimethoxysilylpropyl)-(p-N,N-dimethylamino) benzamide and 10 g of phenyltrimethoxysilane were dissolved in 100 mL of methanol and mixed with 300 mL of water which was being stirred at 40° C. to obtain a colloid. After adding 30 mL of 10% NaOH aqueous solution and stirring overnight, pH was adjusted to 5-6 using concentrated hydrochloric acid and particles were recovered by filtering.

Example 25

Preparation of Particles Using (Trimethoxysilylpropyl)-(P-N,N-Dimethylamino)Benzamide and Methyltrimethoxysilane 10 g of (trimethoxysilylpropyl)-(p-N,N-dimethylamino) benzamide and 1 g of methyltrimethoxysilane (Aldrich) were added to 200 mL of 1 wt % NaOH aqueous solution at 60° C. while vigorously stirring. The resulting colloidal solution was stirred for 12 hours and pH was adjusted to 5-6 using 10 wt % HCl. After further stirring for 2 hours, particles were recovered by filtering. The obtained particles were insoluble to ethanol, acetone, methanol, etc. and thus were suitable as insoluble UV-blocking particles.

Example 26

UV Absorption Spectrum of Particles Prepared Using (Trimethoxysilylpropyl)-(P-N,N-Dimethylamino)Benzamide and Methyltrimethoxysilane 0.01 wt % colloidal aqueous solution was prepared using the particles obtained Example 25 and UV absorbance was measured between 600 nm and 250 nm. A spectrum similar to that of p-N,N-dimethylbenzoic acid was obtained.

Example 27

UV Stability of Particles Prepared Using (Trimethoxysilylpropyl)-(P-N,N-Dimethylamino)Benzamide and Methyltrimethoxysilane UV absorbance of the particles obtained in Example 25 was measured as in Example 5. After irradiation of UV for 30 minutes, 1 hour, 1.5 hours, 2 hours and 3 hours, the particles exhibited very superior UV stability, with 97% 95%, 90%, 90% and 85% of initial absorbance, respectively.

Example 28

UV Stability of Particles Prepared Using N-(Trimethoxysilylpropyl)-(P-N,N-Dimethylamino)Benzamide and Methyltrimethoxysilane 2

Figure 7:
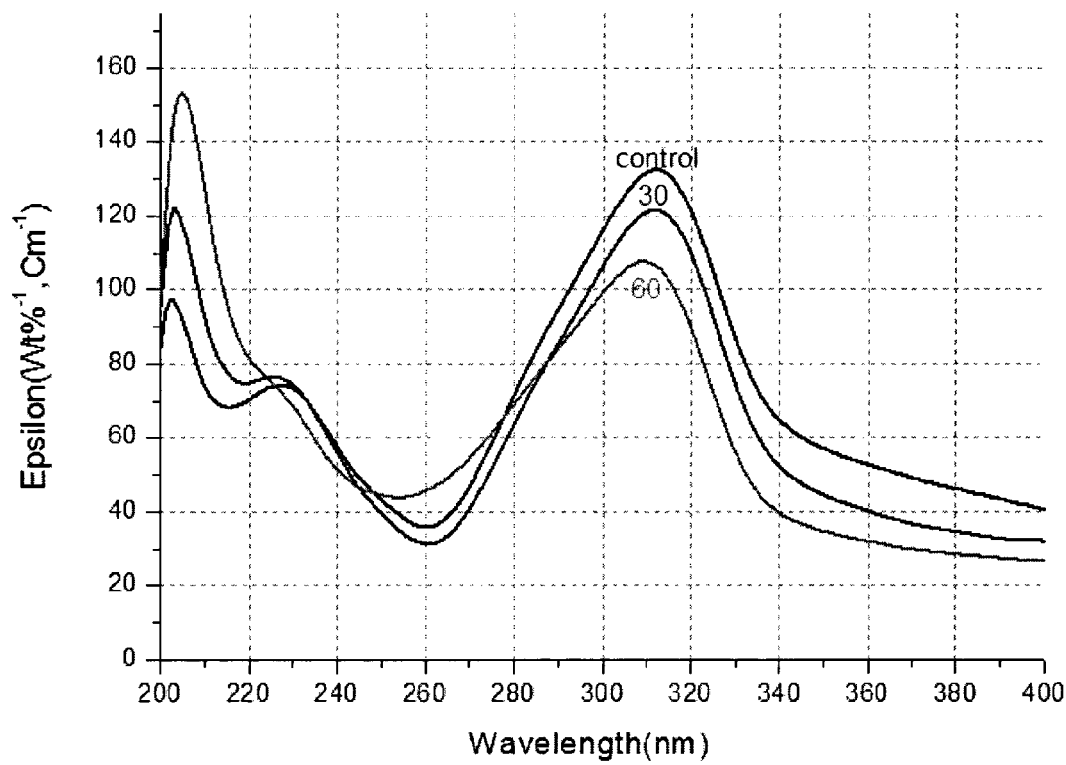
FIG. 7 shows an absorbance analysis result of particles prepared from (methyldimethoxysilylpropyl)-(p-N,N-dimethylamino)benzamide and methyltrimethoxysilane showing their UV stability.

0.02 wt % colloidal solution was prepared using the particles obtained Example 25 and UV absorbance was measured after irradiation of UV for 30 minutes, 1 hour and 2 hours. The particles exhibited good UV stability, with 89% and 81% of initial absorbance (FIG. 7).

Example 29

Preparation of Particles Using N-(Methyldimethoxysilylpropyl)-(P-N,N-Dimethylamino)Benzamide and Methyltrimethoxysilane 5 g of N-(methyldimethoxysilylpropyl)-(p-N,N-dimethylamino)benzamide and 10 g of methyltrimethoxysilane were mixed and added to 800 mL of 0.1t % NaOH aqueous solution at 60° C. The resulting colloid was stirred for 12 hours at room temperature and pH was adjusted to 5-6 using 10 wt % HCl. After further stirring for 2 hours, particles were recovered by filtering.

Example 30

UV Stability of Particles Prepared Using (Methyldimethoxysilylpropyl)-(P-N,N-Dimethylamino) Benzamide and Methyltrimethoxysilane UV absorbance of the particles obtained in Example 29 was measured as in Example 5. After exposure to UV for 30 minutes and 1 hour, the particles exhibited superior UV stability, with 93% and 85% of initial absorbance, respectively.

Example 31

Synthesis of Hydroxymethyltriethoxysilyl-(P-Methoxycinnamate)

100 g of p-methoxycinnamic acid (Aldrich) was dissolved in 500 mL of toluene and 118 g of dicyclohexylcarbodiimide (DCC) (Aldrich) was added. After adding 100 g of hydroxymethyltriethoxysilane (Gelest), the toluene solution was stirred for about 18 hours at about 40° C. After evaporating the solvent under reduced pressure and adding 200 mL of acetone, insoluble byproduct (dicyclohexylurea) was removed by filtering. After removal of acetone, triethoxysilylmethyl-(p-methoxycinnamate) was obtained. The new product could be identified by thin-layer chromatography.

Example 32

Preparation of Particles Using Triethoxysilylmethyl-(P-Methoxycinnamate) and Methyltrimethoxysilane 20 g of the product obtained in Example 31 was mixed 10 g of methyltrimethoxysilane (Aldrich) to prepare a homogeneous solution. After adding the solution to 2 L of 5% ammonia aqueous solution which was being vigorously stirred, the mixture was vigorously stirred for 24 hours. After recovering particles by centrifugation, they were washed twice with ethanol and then dried.

Example 33

Compatibility of Particles Prepared Using Trimethoxysilylpropyl-P-Methoxycinnamamide and Propyltrimethoxysilane 10 g of the particles prepared in Example 15 using trimethoxysilylpropyl-p-methoxycinnamamide and propyltrimethoxysilane were vigorously mixed with 40 g of petrolatum and applied on hands with about 2 mg/cm2. No white turbidity occurred.

Example 34

Compatibility of Particles Prepared Using Trimethoxysilylpropyl-P-Methoxycinnamamide and Phenyltrimethoxysilane 10 g of the particles prepared in Example 18 using trimethoxysilylpropyl-p-methoxycinnamamide and phenyltrimethoxysilane (Aldrich) were vigorously mixed with 20 g of petrolatum and applied on hands with about 2 mg/cm2. No white turbidity occurred.

Example 35

Compatibility of UV-blocking Particles Prepared Using N-(Trimethoxysilylpropyl)-(P-N,N-Dimethylamino)Benzamide and Methyltrimethoxysilane 10 g of the particles prepared in Example 25 using N-(trimethoxysilylpropyl)-(p-N,N-dimethylamino)benzamide and methyltrimethoxysilane (Aldrich) were vigorously mixed with 20 g of petrolatum and applied on hands with about 2 mg/cm2. No white turbidity occurred.

Example 36

Preparation of Particles from Trimethoxysilylpropyl-P-Methoxycinnamamide and Dimethyldimethoxysilane 10 g of trimethoxysilylpropyl-p-methoxycinnamamide and 10 g of dimethyldimethoxysilane were dissolved in 5 g of ethanol and added at once to 2 L of 5% ammonia aqueous solution which was being stirred at 40° C. After stirring for 24 hours and adjusting pH to 6 using 5% hydrochloric acid aqueous solution, particles were recovered by filtering.

Example 37

Comparison of Hardness of Particles Prepared from Trimethoxysilylpropyl-P-Methoxycinnamamide with Particles Prepared from Trimethoxysilylpropyl-P-Methoxycinnamamide and Dimethyldimethoxysilane 1

When the particles prepared in Example 36 and those prepared in Example 2 using trimethoxysilylpropyl-p-methoxycinnamamide were rubbed with fingers, the particles obtained in Example 36 lumped like an eraser.

Example 38

Comparison of Hardness of Particles Prepared from Trimethoxysilylpropyl-P-Methoxycinnamamide with Particles Prepared from Trimethoxysilylpropyl-P-Methoxycinnamamide and Dimethyldimethoxysilane 2

Figure 8:
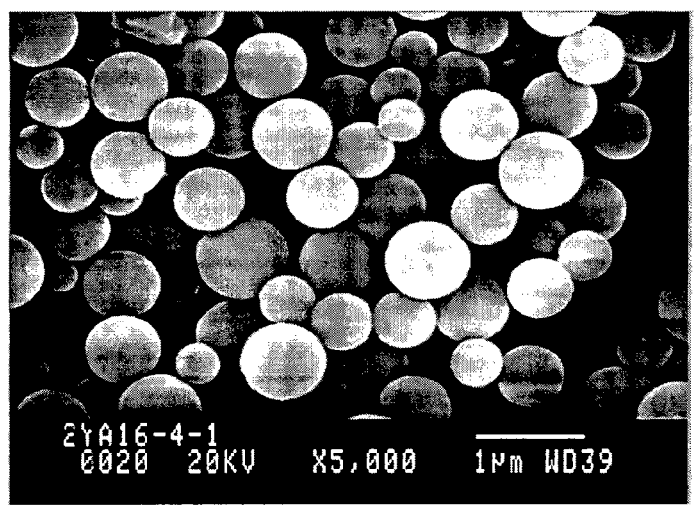
FIG. 8 is an SEM image of particles prepared from specific trimethoxysilylpropyl-p-methoxycinnamamide.
Figure 9:
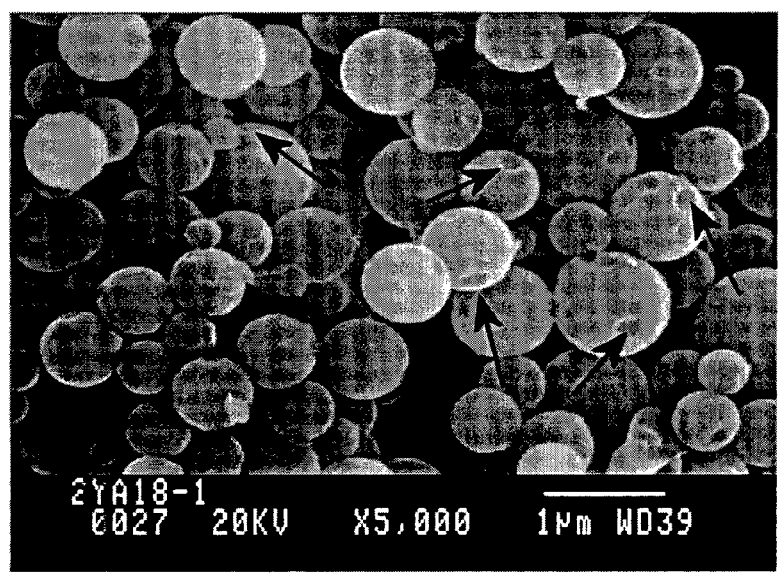
FIG. 9 is an SEM image of particles prepared from the trimethoxysilylpropyl-p-methoxycinnamamide used for preparation of the particles of FIG. 8 and dimethyldimethoxysilane. When compared with the FIG. 8, it can be seen that dried neighboring particles are detached due to week hardness, resulting in tearing.

SEM images of the particles prepared only with trimethoxysilylpropyl-p-methoxycinnamamide in Example 37 and the particles prepared in Example 36 were compared (FIG. 8 and FIG. 9). The particles of Example 36 showed tearing show tearing caused by detachment of neighboring particles due to week hardness (FIG. 9), whereas the particles prepared only with trimethoxysilylpropyl-p-methoxycinnamamide did not show such damage. Accordingly, it can be seen that the particles prepared in Example 36 have weaker hardness.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for preparing poly(organic oxidized silicon) particles having UV-absorbing groups, comprising reacting an organoalkoxysilane precursor having a UV-absorbing group selected from a group consisting of organotrialkoxysilane, diorganoalkoxysilane and a mixture thereof, in the presence of a base, with a silane compound selected from a group consisting of aryltrialkoxysilane, diaryldialkoxysilane, arylalkyldialkoxysilane and a mixture thereof, serving as a crosslinking regulator and UV stability enhancer, so as to prepare poly(organic oxidized silicon) particles selected from a group consisting of polysilsesquioxane, silsesquioxane-siloxane copolymer, silsesquioxane-silica copolymer, silsesquioxane-siloxane-silica copolymer and silsesquioxane-siloxane copolymer, having UV-absorbing groups.

2. The method according to claim 1, wherein the UV-absorbing group is cinnamic acid or an alkoxy derivative thereof, benzoic acid or an ester thereof, p-aminobenzoic acid or a derivative thereof, benzylidenecamphor or a derivative thereof, isophthalylidenecamphor, terephthalylidenecamphor, salicylic acid or an ester thereof, a coumarin-based UV-absorbing group, 2-arylbenzimidazole, 2-arylbenzofuran, 2-arylbenzoxazole or 2-arylindole.

3. The method according to claim 2, wherein the UV-absorbing group is p-methoxycinnamic acid or N,N-dimethyl-p-aminobenzoic acid.

4. The method according to claim 1, wherein the organoalkoxysilane precursor is alkyltrialkoxysilane or aryltrialkoxysilane having a UV-absorbing group, the crosslinking regulator and UV stability enhancer is alkyltrialkoxysilane or aryltrialkoxysilane, and the poly(organic oxidized silicon) having a UV-absorbing group is polysilsesquioxane having a UV-absorbing group.

5. The method according to claim 1, wherein the base is a strong base selected from a group consisting of NaOH, KOH, $Ca(OH)_2$, $Ba(OH)_2$, CsOH, $Sr(OH)_2$, LiOH, RbOH, $Mg(OH)_2$, triethylamine and ammonia.

6. The method according to claim 1, which further comprises, after the reaction between the poly(organic oxidized silicon) precursor and the crosslinking regulator, adjusting pH to 5-8.

7. Poly(organic oxidized silicon) particles having UV-absorbing groups prepared by any of the methods according to claim 1.

8. A cosmetic composition for blocking UV, comprising the poly(organic oxidized silicon) particles having UV-absorbing groups according to claim 7.

9. The method according to claim 1 wherein the covalent bonding between the UV-absorbing group and the alkyltrialkoxysilane, dialkyldialkoxysilane, diaryldialkoxysilane or aryltrialkoxysilane is an amide or ester bonding via the amino group or hydroxyl group at the end of the alkyltrialkoxysilane, dialkyldialkoxysilane, diaryldialkoxysilane or aryltrialkoxysilane.

10. The method according to claim 9, wherein the organoalkoxysilane precursor having a UV-absorbing group is trialkoxysilylalkyl-p-methoxycinnamamide, alkyldialkoxysilylalkyl-p-methoxycinnamamide, trialkoxysilylaryl-p-methoxycinnamamide, trialkoxysilylalkyl-p-methoxycinnamic acid ester, alkyldialkoxysilylalkyl-p-methoxycinnamic acid ester, trialkoxysilylaryl-p-methoxycinnamic acid ester, (trialkoxysilylalkyl)-(p-N,N-dimethyl-p-amino)benzamide, (alkyldialkoxysilylalkyl)-(p-N,N-dimethyl-p-amino)benzamide, (trialkoxysilylaryl)-(p-N,N-dimethyl-p-amino)benzamide, (trialkoxysilylalkyl)-(p-N,N-dimethyl-p-amino)benzyl ester, (alkyldialkoxysilylalkyl)-(p-N,N-dimethyl-p-amino)benzyl ester or (trialkoxysilylaryl)-(p-N,N-dimethyl-p-amino)benzyl ester.

11. The method according to claim 10, wherein the silsesquioxane precursor having a UV-absorbing group is trialkoxysilylalkyl-p-methoxycinnamamide and the crosslinking regulator and UV stability enhancer is aryltrialkoxysilane, arylalkyldialkoxysilane or diaryldialkoxysilane.

12. The method according to claim 10 wherein the silsesquioxane precursor having a UV-absorbing group is trialkoxysilylalkyl-p-methoxycinnamamide and the crosslinking regulator and UV stability enhancer is a mixture of aryltrialkoxysilane and alkyltrialkoxysilane.

* * * * *